United States Patent [19]

Anello et al.

[11] 4,124,606

[45] Nov. 7, 1978

[54] SULFONATION OF ANTHRAQUINONE IN SULFUR DIOXIDE SOLVENT

[75] Inventors: Louis G. Anello, Hamburg, N.Y.; Morris B. Berenbaum, Summit, N.J.; James O. Peterson, Sylvania, Ohio; Bernard Sukornick; Allen W. Sogn, both of Williamsville, N.Y.

[73] Assignee: Buffalo Color Corporation, West Paterson, N.J.

[21] Appl. No.: 748,433

[22] Filed: Dec. 8, 1976

[51] Int. Cl.$^2$ .................................................. C09B 3/02
[52] U.S. Cl. ..................................... 260/370; 260/686
[58] Field of Search ............................... 260/686, 370

[56] References Cited

U.S. PATENT DOCUMENTS

| 1,963,383 | 6/1934 | Rogers | 260/370 |
| 2,244,512 | 6/1941 | Brandt | 260/686 X |
| 2,706,736 | 4/1955 | Birch et al. | 260/686 X |
| 2,863,912 | 12/1958 | Smith | 260/686 X |
| 3,792,065 | 2/1974 | Hiller et al. | 260/370 |

*Primary Examiner*—Allen B. Curtis
*Attorney, Agent, or Firm*—Michael L. Dunn

[57] ABSTRACT

Sulfonation of anthraquinone by a sulfur trioxide component including $SO_3$ or oleum in a liquid sulfur dioxide solvent. When a mercury catalyst is used to give alpha anthraquinone sulfonate products, most of the mercury is left in the reactor or recovered with unreacted anthraquinone by precipitation with water after vaporization of the sulfur dioxide. High sulfuric acid and mercury pollution are thus avoided.

22 Claims, No Drawings

SULFONATION OF ANTHRAQUINONE IN SULFUR DIOXIDE SOLVENT

BACKGROUND OF THE INVENTION

This invention relates to novel methods for the sulfonation of anthraquinones, and particularly to the sulfonation of anthraquinone in a sulfur dioxide solvent.

Anthraquinone derivatives are among the leading dyestuffs used commercially. Many of these derivatives are produced by processes beginning with the sulfonation of anthraquinone to form monosulfonic acids, disulfonic acids, mixtures thereof and salts thereof. Such monosulfonic acids include principally 1-anthraquinonesulfonic acid (alpha), 2-anthraquinonesulfonic acid (beta). Disulfonic acids include anthraquinone-1,5-disulfonic acid, anthraquinone-1,8-disulfonic acid (alpha), anthraquinone-2,6-disulfonic acid and anthraquinone-2,7-disulfonic acid (beta). Anthraquinone-1,7-disulfonate, and other possible anthraquinone sulfonates or disulfonates are not usually formed in significant quantities.

Sulfonation of anthraquinone is normally conducted by adding anthraquinone to oleum (fuming sulfuric acid) as solvent and reagent and a catalyst such as mercury (usually as the sulfate) and/or boric acid. Sulfonation without a mercury catalyst gives beta acids almost exclusively (2-sulfonic, 2,6-disulfonic and 2,7-disulfonic) while addition of small amounts of mercury is known to give alpha subsitution (1-sulfonic, 1,5-disulfonic and 1,8-disulfonic).

After sulfonation with oleum, the sulfonic acid is conventionally quenched by drowning the batch in water and precipitating the acid as an alkali metal salt. Examples of such processes are disclosed in: U.S. Pat. Nos. 2,742,484, 2,900,397, 2,999,869, and 3,079,404; British Pat. Nos. 1,314,120 and 1,339,114; French Pat. No. 2,139,530; German Pat. No. 2,163,674; Organic Chemistry of Sulfur by C. M. Suter, pages 302 to 305 and Kirk-Othmer, Encyclopedia of Chemical Technology, pages 439 to 447. United States Patent Nos. 2,074,307 and 2,074,309 report a lesser dilution of the batch with water and precipitation of the acid as the oxonium salt.

Sulfonation with oleum as both the sulfonating agent and the solvent presents serious pollution and economic disadvantages. Substantial amounts of sulfuric acid are discarded in dilute form after precipitation of the sulfonates. Particularly after the preparation of the alpha sulfonates 1-, 1,5- and 1,8-, where mercury catalyst is used, the sulfuric acid by-product is contaminated with mercury which makes it both unusable in other processes and extremely polluting if discharged into waterways. Attempts to remove the mercury impurities are both expensive and, in some cases, incomplete.

BRIEF DESCRIPTION OF THE INVENTION

The present invention includes sulfonation of anthraquinone by reacting anthraquinone and a sulfur trioxide component of $SO_3$ or oleum in a liquid sulfur dioxide solvent.

In preferred forms, the reaction mixture is held for a reaction period of between about 1 and about 20 hours, and preferably between about 1 and about 6 hours, at temperatures between about 60° C. and about 160° C., and more preferably between about 80° C. and about 135° C. and most preferably between about 110° C. and about 130° C., under sufficient pressures for the sulfur dioxide solvent to be liquid. The anthraquinone sulfonates or salts thereof are then recovered from the reaction mixture.

In some preferred forms, the reaction mixture includes a mercury catalyst, generally mercuric sulfate, such that the predominant products are alpha sulfonates. Also in preferred forms, the sulfur dioxide is removed after the reaction period by vaporization, and unreacted anthraquinone is recovered by precipitation upon the addition of water. Most of the mercury catalyst, if any, is recovered as a solid precipitate in the reaction chamber or upon filtration or with the unreacted anthraquinone and recycled therewith. Sulfuric acid and mercury pollution are thereby minimized.

DETAILED DESCRIPTION OF THE INVENTION

The present invention includes the sulfonation of anthraquinone by a sulfur trioxide source which is $SO_3$ or oleum in a liquid sulfur dioxide solvent. When the alpha monosulfonate anthraquinone-1-monosulfonic acid or salts thereof is desired, a mercury catalyst is used and the preferred sulfur trioxide source is preferably substantially anhydrous $SO_3$. When the alpha disulfonates, anthraquinone-1,5-disulfonic, anthraquinone-1,8-disulfonic acids and salts thereof are desired, mercury catalyst is used and the sulfur trioxide source is preferably oleum. When the beta monosulfate, anthraquinone-2-monosulfonic acid or salts thereof, is desired, no mercury catalyst is used and the sulfur trioxide source is preferably substantially anhydrous $SO_3$. When the beta disulfonates, anthraquinone-2,6-disulfonic acid and anthraquinone-2,7-disulfonic acid, are desired, no mercury catalyst is used and oleum is the preferred sulfur trioxide source.

The reaction mixture includes sulfur dioxide as solvent. The amount of sulfur dioxide is not critical, so long as sufficient sulfur dioxide is present to dissolve the reactants. About 5% to about 30% solids by weight of composition is preferred. The sulfur dioxide may conveniently be introduced into the reaction chamber in liquid form by cooling, pressurization or both. If the sulfur dioxide is initially in liquid form, as is preferred, and the reaction vessel is closed, sufficient pressure will be attained by heating the reaction vessel to the desired reaction temperature to maintain the sulfur dioxide solvent predominately as a liquid.

If, instead, the sulfur dioxide solvent is introduced in gaseous form, pressurization of the reaction chamber may be required to achieve substantial liquid sulfur dioxide solvent at reaction temperatures.

The sulfur trioxide reaction component may be either $SO_3$ or fuming sulfuric acid (oleum).

By "oleum" is meant sulfur trioxide-containing sulfuric acid. In general, if one starts with one mole of water, addition of sulfur trioxide up to about 0.95 to 0.98 moles produces sulfuric acid and no unbound sulfur trioxide. For simplicity, it shall be assumed that 100% sulfuric acid is formed with one mole of sulfur trioxide, although this is only an approximation. After one mole of sulfur trioxide, all additional sulfur trioxide can be considered "excess" as it is not converted from the oxide to the acid. Oleum is quantified by weight % of "excess" $SO_3$ by total weight of oleum. Small excesses will not freely "fume" or vaporize as $SO_3$, and large excesses will hardly be associated with the sulfuric acid at all. Nonetheless, all mixtures of sulfuric acid and excess sulfur trioxide can be considered "oleum." To avoid substantial amounts of water in the first separation steps downstream from the reaction chamber, it is generally preferred to use a minimum water content in the sulfur trioxide component.

For the production of monosulfonates, substantially anhydrous $SO_3$ is preferred. Oleum with a large excess of sulfur trioxide may also be used, however. For the production of disulfonates, oleum with an excess sulfur trioxide content of about 50% to about 70%, by weight, is preferred. In general, reaction mixtures using oleum below about 50% excess sulfur trioxide can cause unnecessarily high water content downstream, and may have insufficient sulfur trioxide for the initial sulfonation of anthraquinone. Oleum with between about 70% and 95% excess sulfur trioxide, by weight, appears to give only partial sulfonation of anthraquinone monosulfonic acids to disulfonic acids. Oleum with over about 95%, by weight, of excess sulfur trioxide, up to anhydrous sulfur trioxide, gives almost exclusively monosulfonic acids. This general observation may be used to improve selectivity: by choosing oleum with under about 70% excess sulfur trioxide if disulfonates are desired, but choosing oleum with over about 95% excess sulfur trioxide when monosulfonates are desired. Of course, substantially anhydrous sulfur dioxide with only negligible water content falls within the definition of oleum with over 95% excess sulfur trioxide.

To achieve disulfonation, sufficient amounts of reactive sulfur trioxide must also be present. At least two moles of reactive sulfur trioxide are required per mole of anthraquinone (stoichiometric proportions). Sulfur bound to water as sulfuric acid may be disregarded such that only the excess sulfur trioxide in oleum is reactive. Preferably, reactive sulfur trioxide in excess of stoichiometric proportions is used, with about 50% to a 200% excess, that is about 3:1 to about 6:1 molar ratio of reactive or excess sulfur trioxide to anthraquinone are used. Excess sulfur trioxide over a 6:1 molar ratio to anthraquinone does not appear to increase yields and adds to the sulfuric acid amounts in the effluent.

When monosulfonation is desired, molar ratios of reactive sulfur trioxide to anthraquinone of about 1:1 to about 3:1 are preferred. Excesses over 3:1 molar ratios do not appear to improve yields, but normally do not result in undesired disulfonation in the absence of water or sulfuric acid.

In sulfur dioxide solvent, catalysts are not normally required to produce beta sulfonates: anthraquinone-2-sulfonic acid, anthraquinone-2,6-disulfonic acid and anthraquinone-2,7-disulfonic acids. In each of these forms, substitution occurs only of the four beta sites 2, 3, 6 and 7 not adjacent to the inter-ring carbons.

As with sulfonation in aqueous solvent, addition of small amounts of mercury catalyst, preferably as a sulfate, causes alpha substitution at the sites adjacent the inter-ring carbons, that is in the 1, 4, 5 or 8 position. The alpha monosulfonate, anthraquinone-1-monosulfonic acid, is formed under monosulfonation conditions such as with a substantially anhydrous sulfur trioxide reactant. The alpha disulfonates, anthraquinone-1,5-disulfonic acid and anthraquinone-1,8-disulfonic acid, are formed under disulfonation conditions such as oleum with about 50% to about 70% excess sulfur trioxide, by weight, as the sulfur trioxide reactant.

Very small amounts of mercury are sufficient to cause alpha substitution, and substantial amounts could be used without changing the reaction product. Nevertheless, at least about 0.05% by weight of mercury to weight of sulfur dioxide solvent is preferred to assure that beta sulfonates will not be produced in significant amounts. Usually with 0.05% mercury, the product contains no easily measurable beta sulfonate impurities. Mercury concentrations above about 1.0% by weight of mercury to weight of sulfur dioxide solvent are unnecessary. Thus, the preferred range of mercury catalyst by weight of mercury to weight of solvent is about 0.05% to about 1.0%.

As should be apparent, an active mercury catalyst of mercuric ions or mercuric sulfate will be formed from almost any inorganic mercury compound and many organic mercury compounds in an environment of high sulfate, sulfur trioxide or both. So long as the mercury is not covalently bound by bonds which are not broken in such an environment, most any form of mercury may be used as the catalyst. In such small amounts as are contemplated in the present process, it is unlikely that other parts of the mercury compounds would poison the catalyst or otherwise interfere with the reaction.

To avoid extra components in the effluent, mercuric sulfate is the preferred mercury catalyst. Mercury salts other than $HgSO_4$ could be used, but the sulfate is preferred for simplicity to avoid additional components in the effluent.

Of course the mercury catalyst could be introduced as metallic mercury, such salts as the nitrate, halide, oxide or chlorate or as a mercury ester or the like.

Other catalysts can be used, but are not generally required. For beta sulfonate products, no catalyst appears necessary.

The methods of introducing reactants into the reaction chamber are varied. Sulfur trioxide may conveniently be mixed with some of the sulfur dioxide solvent. The mercury catalyst may be introduced in dry form. The anthraquinone reactant may be dissolved in some of the sulfur dioxide or introduced in dry form as well.

For selective production of lower sulfonates, the reaction is preferably conducted at a reaction temperature of between about 60° C. and about 160° C., and more preferably between about 80° C. and about 135° C. and most preferably between about 110° C. and 130° C. Of course, the reaction mixture may be maintained at varied temperatures including one or more periods at a temperature or temperatures within the preferred range. However, excessive temperatures may cause oversulfonation of the anthraquinone and loss of selectivity. For example, temperatures over 130° C. or 135° C. may cause increasing amounts of di- or tri-sulfonates to be formed when monosulfonation is desired and tri- and higher sulfonates to be formed when disulfonation is desired.

The reaction mixture should preferably be kept at reaction temperatures until further net reaction substantially ceases, which occurs before about twenty hours and generally before about 6 hours. Reaction times between about 1 and 20 hours are preferred, and reaction times between about 1 and about 6 hours are more preferred since the reaction is normally essentially complete within those times. Longer reaction times are possible, but generally do not improve yields.

As stated above, the reaction pressure should be sufficient to avoid sulfur dioxide boil off by maintaining a pressure sufficient to keep the sulfur dioxide liquid. Preferably, the reaction mixture in the reaction chamber is almost entirely in the liquid phase.

The advantages of sulfonation of anthraquinone in sulfur dioxide solvent should be apparent from the preferred separation techniques described herein. However, any techniques that take advantage of the properties of sulfur dioxide can be used.

In preferred forms, the reaction chamber is emptied after the reaction period and filtered with an acid-proof membrane to remove undissolved mercury sulfate which is returned to the reaction chamber. The filtrate is placed in a receiver and the pressure is lowered so that the sulfur dioxide solvent may gasify, to be recycled to the reactor if desired. A nitrogen purge removes residual sulfur dioxide. The crude product will precipitate forming a slurry.

The crude product is then removed to a separation chamber. Addition of small amounts of warm water to the crude product causes the crude product to be solubilized and the unreacted anthraquinone to precipitate after cooling. Filtration removes the solid anthraquinone which can be recycled after drying.

As shown in Example 9 below, most of the mercury remains in the reactor as insoluble metallic mercury or mercury sulfate. Much of the remaining mercury is found in the filter precipitate before gassification. As shown in Example 10, much of the remaining mercury is recycled with the unreacted anthraquinone. Very little mercury remains in the filtrate at this point.

The anthraquinone sulfonic acids may then be precipitated and recovered as salts by addition of an inorganic salt to the filtrate. Many inorganic salts, oxides or hydroxides may be added to cause the sulfonated anthraquinones to become salts which are insoluble in such highly concentrated sulfuric acid solutions. For example, the sulfates, halides, hydroxides and nitrates of alkali metals may be used. Appropriate salts include, as examples, LiI, NaBr, KF, RbCl, $K_2SO_4$ and NaOH.

Some alkaline earth or transition metal salts may also be used. However, in the concentrated sulfuric acid environment to which the salt is added, many metals such as iron, calcium and barium form insoluble sulfate salts that would precipitate with or instead of the anthraquinone sulfonate salts. Bromide and iodide ions might be oxidized to elemental bromine and iodine which could complicate further separation.

Nitrates, chlorides and fluorides would add additional ions to the solution, but they are still preferred as the anions remain soluble and thus do not complicate the system. Oxides, hydroxides and sulfates are preferred also since only more water and sulfate ions are added to the system. Some oxides and hydroxides may, however, be slightly less preferred than the sulfates because of the heat evolved by neutralization.

Thus the most preferred salts, oxides and hydroxides are the fluorides, chlorides, nitrates, sulfates and hydroxides of alkali metals. Other salts, oxides and hydroxides that produce no insoluble component are also highly preferred. Salts, oxides and hydroxides that produce insoluble components in addition to the anthraquinone sulfonate salts are less preferred, but may be used. Salts, oxides and hydroxides that do not precipitate anthraquinone sulfonate salts would not be used. Saturated aqueous salt solution are preferred. Crude alkali anthraquinone sulfonate precipitates and can be recovered by a second filtration.

The filtrate contains relatively concentrated unreacted sulfuric acid and the inorganic salt, and may be neutralized and discarded, or the sulfuric acid may be recovered by known techniques. In any case, the amounts of sulfuric acid from unreacted sulfur trioxide reactant is much smaller than that from the reactant and solvent oleum left in prior art processes. Additionally, the mercury content is quite low.

The crude anthraquinone sulfonate salts may then be washed with dilute inorganic salts, preferably the same salt as before, to remove residual sulfuric acid. The product may then be dried.

Of course acid-resistant chambers, conduits and filters should be used throughout.

EXAMPLES 1–5

Preparation of 1-Anthraquinone Sulfonic Acid

EXAMPLE 1

Into a 1 gal. stainless steel jacketed reactor provided with an agitator were charged 312g. (1.5 moles) of anthraquinone, and 4.5g (1.0% as Hg) of mercuric sulfate. In the meantime, 3.5 lbs. of sulfur dioxide were condensed in a previously cooled jacketed feedtank which has an agitator and cooling coils for temperature control. After all the sulfur dioxide was charged, the feedtank was warmed to room temperature and the liquid sulfur dioxide was pumped to the sealed reactor by means of a Lapp pump. At the end of the pumping operation the reactor pressure gauge registered 36 psig (pressure of $SO_2$ at 25° C.). With agitation, the reactor was heated to 120° C. for one half-hour. In the meantime, the feedtank was recharged with an additional 2.7 lbs of $SO_2$ and also with 170g. (2.12 moles) of sulfur trioxide and mixed. (The sulfur trioxide was dropped into the feedtank from a 500 ml s.s. container). The $SO_3/SO_2$ mixture was slowly fed to the reactor which was heated at 120° C. and 575 psi over a 2 hour period. The reactor temperature was then raised from 120° C. to 130° C. and held at 130° C. and 630 psi for 4 hours. The reactor was then cooled to 60° C. and the product mixture discharged thru the heated filter unit (filter unit contained TFE filter membrane of 5 to 10 micron pore size) to the receiver where the crude product precipitated from the $SO_2$ solution as it cooled and the $SO_2$ was vented to a caustic scrubber. After all the $SO_2$ was vented, the receiver was purged with nitrogen and the product removed from the receiver.

The recovered product was added to sufficient distilled water to effect solubilization. The solution was heated to 70° C. over a one hour period, cooled to 25° C. and filtered to recover unreacted anthraquinone. The filtrate was transferred to a beaker and the sulfonic acid derivative was precipitated by addition of a 25% solution of potassium chloride. The sulfonic acid potassium salt was isolated by filtration and further washed with a 2% potassium chloride solution, then dried along with the recovered unreacted anthraquinone in a vacuum oven. The yield of potassium salt was 394g. (1.2 moles, 88% yield) with 26.5g. (0.13 mole) unreacted anthraquinone recovered (91% conversion).

EXAMPLE 2 — Analysis of Product

To determine the purity or strength of the product in Example 1, the salt was converted to the chloroanthraquinone derivative by adding sodium chlorate to an acid solution of the potassium sulfonate. The reaction proceeds as shown in the equation below:

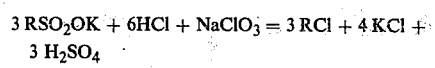

A sample of the potassium salt isolated above was converted to the 1-chloroanthraquinone derivative. The melting point found was 161°–162° C., consistent with reported melting points of 1-chloroanthraquinone.

EXAMPLE 3

Into the reactor described in Example 1 were charged 312g. (1.5 mole) of anthraquinone, 0.45g. (0.1% as Hg) of Hg SO$_4$ and 3.5 lbs of sulfur dioxide. The mixture was heated to 120°–125° C. Then 170g. (2.12 moles) of SO$_3$ in 2.8 lbs of SO$_2$ were mixed and charged over a 2 hour period to the reactor, after which the reactor was maintained at 130° C. for 4 hours with agitation. The reactor was cooled to room temperature, the SO$_2$ solvent was vented and the product solubilized in water and discharged from the reactor. There was recovered 326.8g. (1.13) mole of crude 1-anthraquinone sulfonic acid and 39.4g. (0.19) of unreacted anthraquinone. The yield of 1-anthraquinone sulfonic was 86% and conversion was 75.5%.

EXAMPLE 4

Into the reactor described in Example 1 were charged 312g. (1.5 moles) of anthraquinone, 0.225g. (0.05% as Hg) of HgSO$_4$ and 3.5 lbs of sulfur dioxide. The mixture was heated to 120°–125° C. Then 170g. (2.12 moles) of SO$_3$ in 2.8 lbs of SO$_2$ were mixed and charged over a 2 hour period to the reactor, after which the reactor was maintained at 130° C. for 4 hours with agitation. The reactor was cooled to room temperature, SO$_2$ solvent was vented and the product solubilized in water and discharged from the reactor. There was recovered 314g. (1.08 M) of crude 1-anthraquinone sulfonic acid and 87g. (0.42 M) of unreacted anthraquinone. The yield of 1-anthraquinone sulfonic acid was 100% and conversion was 72%.

EXAMPLE 5

Into the reactor described in Example 1 were charged 312g. (1.5 moles) of anthraquinone, 0.112g. (0.025% as Hg) of HgSO$_4$ and 3.5 lbs of sulfur dioxide. The mixture was heated to 120°–125° C. Then 170g. (2.12 moles) of SO$_3$ in 2.8 lbs of SO$_2$ were mixed and charged to the reactor, after which the reactor was maintained at 130° C. for 6 hours with agitation. Contents of the reactor were discharged through the filter to the receiver, where SO$_2$ solvent was vented and the product solubilized in water and discharged from the reactor. There was recovered 314g. (1.07 moles) of crude 1-anthraquinone sulfonic acid and 91g. (0.43 mole) of unreacted anthraquinone. The yield of 1-anthraquinone sulfonic was 100% and the conversion was 72%.

EXAMPLE 6

Preparation of 2-Anthraquinone Sulfonic Acid

Into the reactor described in Example 1 were charged 208g. (1.0 mole) of anthraquinone and 3 lbs of sulfur dioxide. The mixture was heated to 100° C. with agitation. As the temperature approached 120° C., a solution of 112g. (1.4 moles) of sulfur trioxide in 3 lbs of sulfur trioxide were pumped into the reactor over a 2 hour period. The temperature was maintained at 130°–135° C. for an additional 10 hours, after which the mixture was cooled to room temperature and the sulfur dioxide solvent removed by flash evaporation after filtration to the receiver. The product was worked up as described in Examples 1 and 2. There was recovered 79g. (0.38 mole) of unreacted anthraquinone and 1.75g. (0.61 mole) of 2-anthraquinone sulfonic acid. The conversion and yield to 2-anthraquinone sulfonic acid was 61% and 99%, respectively.

A portion of this potassium salt was converted to the chloroanthraquinone form as described in Example 2. The observed melting point of 208°–211° C. is consistent with reported melting points for 2-chloroanthraquinone.

EXAMPLES 7–8

Preparation of Anthraquinone 1,5- and 1,8-Disulfonic Acids

Example 7

Into the reactor described in Example 1 was charged 312g. (1.50 moles) of anthraquinone and 4.5g. of mercuric sulfate catalyst. The reactor was then charged with 3.5 lbs of sulfur dioxide from the feedtank. As the reactor was warmed from 65° C. to 100° C., a mixture of 460g. of 65% oleum and 2.7 lbs of sulfur dioxide were pumped from the feedtank to the reactor over a 3 hour period. After all the oleum-sulfur dioxide mixture was in, the reactor temperature was raised to 130° C. and maintained at that temperature for 11 hours. The reactor was then cooled and water-washed to remove soluble product. There was recovered 1009g. of crude dried product. The acid was converted to the potassium salt. Recovered 640g. (1.45 mole) for a 97% yield. The crude potassium salt was converted to the chloroanthraquinone derivative as in Example 2. Recovered 346g. (1.16 mole) for a 77% overall yield.

EXAMPLE 8

Into the reactor described in Example 1 was charged 312g. (1.5 moles) of anthraquinone, 6.7g. HgSO$_4$ and 3.5 lbs of sulfur dioxide. As the mixture was warmed to 100° C., a mixture of 97g. of 65% oleum, 277g. of sulfur trioxide and 2.8 lbs of sulfur trioxide and 2.8 lbs of sulfur dioxide were pumped from the feedtank to the reactor over a 3 hour period. After all the reactants were in, the reactor temperature was raised to 130° C. and maintained at that temperature for 11 hours. The reactor was then cooled and water-washed to remove soluble product. There was recovered 750g. of crude dried product. The acid was converted to the potassium salt. Recovered 521g. (1.18 mole) for a 78.5% overall yield.

EXAMPLE 9

Mercury Analysis of Sulfonation Products

Samples of reactor wash water, filter cleanings, filter wash water and crude 1-anthraquinone sulfonic acid as prepared in Example 1 were analyzed for mercury content by Neutron Activation Analysis. The results obtained are given in Table I below:

TABLE I

| Sample Description | Gms or Ml Sample | PPM Hg Found | Total Gms Hg | Percent of Total |
|---|---|---|---|---|
| Reactor wash water | 3525 ml | 860 | 3.0315 | 80.0 |
| Filter cleanings | 16.5 gms | 34,300 | 0.5660 | 14.8 |
| Filter wash water | 31.0 gms | 1,606 | 0.0500 | 1.3 |
| Crude 1-anthraquinone sulfonic acid | 438.0 gms | 350 | 0.1550 | 4.0 |
| | | | 3.8005 gms | 100.0 |

The results indicate that when 1% mercury concentration is used as a sulfonation catalyst in liquid sulfur dioxide, about 80% of the mercury remains in the reactor (that portion of mercury sulfate which is insoluble), 16% is collected in the filter unit and 4% is recovered in the crude sulfonic acid product. The mercury in the reactor under normal plant conditions would not be removed but would serve as catalyst for succeeding runs.

EXAMPLE 10

Mercury Analysis of Unreacted Anthraquinone and Product Crude Sulfonic Acid

A sample of crude 1-anthraquinone sulfonic acid as prepared in Example 1 was purified by dissolving the product into warm water with stirring and filtering the desired product from any unreacted anthraquinone. Analysis of the dried recovered unreacted anthraquinone and 1-anthraquinone sulfonic acid product for mercury indicates that substantially more of the mercury (about 65%) is found in the unreacted anthraquinone than in the sulfonic acid profound in the unreacted anthraquinone than in the sulfonic acid product. The results obtained are given in Table II below:

TABLE II

| Sample Description | Gms or Ml Sample | PPM Hg Found | Total Gms Hg | Percent of Total |
|---|---|---|---|---|
| Unreacted anthraquinone recovered by filtration | 22.5 gms | 5260 | 0.1173 | 65.0 |
| 1-anthraquinone sulfonic acid recovered after filtration | 416.0 gms | 150 | 0.0624 | 35.0 |
| | | | 0.1794 | 100.0 |

EXAMPLE 11

Mercury Analysis of Anthraquinone Sulfonate Salt

A sample of purified 1-anthraquinone sulfonic acid as produced in Example 1, which had been reacted with potassium chloride solution to form the potassium salt, was filtered and dried. Analysis of the potassium salt and the potassium salt filtrate for mercury indicate that the mercury content of the potassium salt can be reduced to 91.8 ppm. This is far below the typical mercury content of commercially available alkali metal sulfonic acids which normally contain about 2700 to 4000 ppm mercury. The results obtained are given in Table III below:

TABLE III

| Sample Description | Gms or Ml Sample | PPM Hg Found | Total Gms Hg | Percent of Total |
|---|---|---|---|---|
| Potassium salt of 1-anthraquinone sulfonic acid | 302.0 gms | 91.8 | 0.028 | 46.5 |
| Potassium salt filtrate | 3400 ml | 9.6 | 0.032 | 53.5 |
| | | | 0.060 | 100.0 |
| Plant sample of ammonium anthraquinone sulfonate prepared by oleum sulfonation | — | 2,711 | — | — |
| Laboratory sample of potassium sulfonate prepared by oleum sulfonation | — | 4,079 | — | — |
| Plant sample of -methyl amino anthraquinone | — | 1,731 | — | — |

EXAMPLES 12–25

One mole of anthraquinone is reacted in liquid SO₂ as in Example 1, with the other reactants and amounts shown in Table IV, below, at the temperature and for the period indicated. The effluent is filtered with an acid-proof membrane and allowed to gassify. Excess liquid oleum or SO₃ is removed. The crude product is solubilized with warm water and filtered to recover unreacted anthraquinone. The product is then precipitated with the aqueous solution indicated, filtered and washed with a 1% aqueous solution of the same material. The unreacted anthraquinone, initial precipitate (mercury sulfate), excess liquid oleum or SO₃ and recondensed SO₂ are recycled and additional anthraquinone is added.

Satisfactory yield are obtained of anthraquinone-2-monosulfonate salts in Examples 12–14, of anthraquinone-1-monosulfonate salts in Examples 15–19, of anthraquinone-1,5- and -1,8-disulfonate salts in Examples 20–22 and of anthraquinone-2,6- and -2,7-disulfonate salts in Examples 23–25.

TABLE IV

| Example | oleum SO₃ mols | % excess SO₃* | mols excess SO₃ | Mercury form | Hg/SO wt % | Aqueous solution |
|---|---|---|---|---|---|---|
| 12 | 1.0 | — | — | — | — | sat KCl |
| 13 | 2.0 | — | — | — | — | sat NaF |
| 14 | — | 95 | 2.0 | — | — | 20% LiOH |
| 15 | 1.0 | — | — | sulfate | 0.1 | 20% RbOH |
| 16 | 1.5 | — | — | oxide | 0.5 | 20% KNO₃ |
| 17 | 3.0 | — | — | nitrate | 1.0 | sat KF |
| 18 | — | 98 | 1.5 | chloride | 1.0 | 10% NaOH |
| 19 | — | 95 | 1.0 | sulfate | 0.5 | 25% KCl |
| 20 | — | 70 | 4.5 | metallic | 1.0 | 25% LiNO₃ |
| 21 | — | 60 | 2.0 | sulfate | 0.5 | 20% NaI |
| 22 | — | 70 | 6.0 | sulfate | 0.5 | 25% KBr |
| 23 | — | 70 | 4.5 | — | — | sat KCl |
| 24 | — | 50 | 5.0 | — | — | sat KNO₃ |
| 25 | — | 60 | 3.0 | — | — | 10% KOH |

*The remainder up to 100% is sulfuric acid.

We claim:

1. In a method for producing sulfonated anthraquinones by reacting anthraquinones and a sulfur trioxide member selected from the group consisting of SO₃ and oleum and dissolving the resulting sulfonated anthraquinone in water to separate it from unreacted anthraquinone, the improvement which comprises carrying out said reaction in a reaction mixture comprising anthraquinone, sulfur trioxide member and a liquid sulfur dioxide solvent at a temperature of from about 60° C. to about 100° C. for from about 1 hour to about 20 hours under sufficient pressure for said sulfur dioxide solvent to be liquid; and subsequent to said reaction vaporizing said sulfur dioxide prior to adding sufficient water to dissolve the sulfonated anthraquinone.

2. A method as claimed in claim 1 wherein the reaction temperature is between about 80° C. and 135° C. and the period is from about 1 hour to about 6 hours.

3. A method as claimed in claim 1 wherein the reaction temperature is between about 110° C. and about 130° C.

4. A method as claimed in claim 1 wherein about 1 to about 2 excess moles of sulfur trioxide member as SO₃ or oleum having at least about 95% excess sulfur trioxide, by weight, are reacted with each mole of anthraquinone.

5. A method as claimed in claim 4 wherein about 1 to about 2 excess moles of substantially anhydrous SO₃ are included in the reaction mixture as the sulfur trioxide member.

6. The method of claim 4 wherein sulfur dioxide is recycled after it is vaporized.

7. The method of claim 6 wherein subsequent to vaporization of sulfur dioxide, and prior to adding water, any remaining excess of oleum or $SO_3$ is removed from the reaction mixture.

8. The method of claim 7 wherein any excess oleum or $SO_3$ is removed from the reaction mixture by filtration.

9. The method of claim 7 wherein the sulfur trioxide member is $SO_3$ which is removed from the reaction mixture by vaporization.

10. The method of claim 7 wherein the sulfur trioxide member is recycled.

11. The method of claim 7 wherein subsequent to removal of the sulfur trioxide member, sufficient water is added to the remaining reaction mixture to dissolve the crude product.

12. The method of claim 11 wherein unreacted anthraquinone is removed from the reaction mixture by filtration subsequent to dissolving of the crude product by water.

13. The method of claim 12 wherein unreacted anthraquinone is recycled after drying.

14. The method of claim 13 wherein anthraquinone sulfonates are precipitated from aqueous solution by addition of an inorganic salt, hydroxide or oxide.

15. The method of claim 14 wherein said salt, hydroxide or oxide is an alkali nitrate, sulfate, chloride, fluoride or hydroxide.

16. The method of claim 15 wherein anthraquinone sulfonates are precipitated by addition of KCl.

17. The method of claim 13 wherein the reaction occurs in the presence of a mercury catalyst.

18. The method of claim 17 wherein prior to vaporization of $SO_2$ the reaction mixture is filtered to remove undissolved mercury catalyst.

19. The method of claim 18 wherein essentially all remaining mercury catalyst is separated with unreacted anthraquinone from anthraquinone sulfonic acid product.

20. A method as claimed in claim 1 wherein oleum having between about 50% and about 90% excess sulfur trioxide is included in the reaction mixture as the sulfur trioxide member, said oleum having a molar ratio of excess sulfur trioxide to anthraquinone of about 2:1 to about 6:1.

21. The method of claim 1 wherein the reaction occurs in the presence of a mercury catalyst.

22. The method as claimed in claim 21 wherein the mercury catalyst is $HgSO_4$ and is present at a concentration from about 0.1% to about 1% mercury by weight of solvent.

* * * * *